United States Patent [19]

Wiles et al.

[11] Patent Number: 4,995,960
[45] Date of Patent: Feb. 26, 1991

[54] ELECTROCHEMICAL ELECTRODES

[75] Inventors: Martin C. Wiles; David J. Schiffrin, both of Southampton; David J. Clarke, Salisbury, all of Great Britain

[73] Assignee: Public Health Laboratory Service Board, England

[21] Appl. No.: 381,665
[22] PCT Filed: Nov. 14, 1988
[86] PCT No.: PCT/GB88/00992
§ 371 Date: Sep. 25, 1989
§ 102(e) Date: Sep. 25, 1989
[87] PCT Pub. No.: WO89/04958
PCT Pub. Date: Jun. 1, 1989

[30] Foreign Application Priority Data
Nov. 24, 1987 [GB] United Kingdom ............... 8727497

[51] Int. Cl.5 .................. G01N 27/30; G01N 27/333
[52] U.S. Cl. .................................... 204/418; 204/435
[58] Field of Search ..................... 204/435, 416, 418

[56] References Cited

U.S. PATENT DOCUMENTS 3,598,713 8/1971 Baum et al. ..................... 204/417
4,431,508 2/1984 Brown et al. ..................... 204/418

FOREIGN PATENT DOCUMENTS 0024191 2/1981 European Pat. Off. .
0100988 2/1984 European Pat. Off. .
0186210 7/1986 European Pat. Off. .

Primary Examiner—G. L. Kaplan
Attorney, Agent, or Firm—Kirschstein, Ottinger, Israel & Schiffmiller

[57] ABSTRACT

An electrochemical reference element is proposed having a metal electrode such as silver coated with the tetraphenyl (TPB) salt of the metal. The element may form the internal reference of an ion selective electrode with an ion selective membrane carried directly upon the TPB coating. The element provides a thermodynamically reversible couple suitable for use in a non-aqueous environment.

17 Claims, 3 Drawing Sheets

ELECTROCHEMICAL ELECTRODES

BACKGROUND OF THE INVENTION

1. Field of the Invention

This invention relates to electrochemical electrodes and particularly to electrochemical reference elements for use in solvents other than water.

2. Description of Related Art

A good example of such usage is ion selective electrodes which are based on organic ion exchangers or neutral carriers. The active material can be in liquid form held in an inert porous membrane but more conveniently the active material is incorporated within a suitably plasticised polymer substrate. In the early designs, the half cell was completed by immersing a silver wire in an internal reference solution of the appropriate chloride salt (potassium for a potassium ion selective electrode) forming a silver/silver chloride internal reference electrode. The potential of this half cell is usually measured against a reference electrode, with the silver/silver chloride reference electrode being usually employed. It will be understood that the ionic current/potential across the membrane is thereby converted into an electronic current/potential at the internal reference electrode, which can be measured. The advantages of using a thermodynamically-definable reversible electrode system as the internal reference electrode will be apparent.

There are clear advantages in developing solid state versions of these ion selective electrodes and considerable efforts have been made in developing so-called "coated wire" electrodes. Commonly, the aqueous internal reference solution is incorporated into a hydrophilic polymer layer such as polyvinyl alcohol (PVA). These devices must be very carefully constructed. For example, in order to prevent osmotic effects across the membrane, this must be introduced when the water content of the PVA layer is within a fixed range. Ideally, this requires coating to be carried out at fixed relative humidities.

In some prior proposals, the use of a reversible electrode has been abandoned with, for example, the membrane being coating directly onto platinum. Even though potentials are measured using very high input impedance volt meters, the ionic to electronic currents are still likely to be high enough to cause problems of drift, noise and lack of reproducibility, in the absence of any thermodynamically reversible electrode. Surface oxides and contamination of the metal can also lead to systematic errors.

A further approach that has been adopted in an attempt to solve this problem is the use of oxidation/reduction processes at noble metal electrodes (for example ferrocence/ferrocenium at a platinum electrode). However, whilst this proposal achieves buffering of the electronic part of the couple, this tends to be unstable.

SUMMARY OF THE INVENTION

It is an object of one aspect of this invention to provide an improved ion selective electrode in which the above difficulties are to a significant extent overcome.

Accordingly, the present invention consists in one aspect in an electrochemical reference element suitable for use with an organic liquid, comprising a metal electrode and a solid electrolyte in contact with the electrode, the electrolyte comprising a salt of an organic ion with the metal of the electrode, the salt being substantially insoluble in said organic liquid and the anion being sufficiently soluble in said organic liquid to form an electrochemical couple.

Preferably, said anion has a hydrophobic aromatic group.

One class of anions comprises anions derived from aryloxyborates, i.e. anions of the general formula $(ArO)_4^-B^+$, wherein each ArO group, which may be the same or different, represents an aryloxy group having up to 20 carbon atoms, optionally substituted by one or more halogen atoms or nitro groups. The aryl group Ar may for example be a phenyl or naphthol group which may be substituted by one or more hydrocarbyl groups having up to 6 carbon atoms. In a particularly preferred class of compounds, Ar is selected from phenyl and 4-halo phenyl.

Another class of anions includes anions derived from hydroxy-substituted aromatic compounds, for example phenols and substituted phenols and naphthols and substituted naphthols. Such compounds include mono-hydroxy phenols and mono-hydroxy naphthols each of which may contain one or more electron-withdrawing groups, for example $NO_2$ groups, as in picrate anions and picraminate anions.

Preferably the metal is selected from the group consisting of silver, cadmium, cobalt, iron, lead and nickel.

The reference element according to this invention may be used within an ion selective electrode with the solid electrolyte establishing contact with an ion selective membrane.

Problems occur with the silver/silver chloride electrode (and the other commonly used reference electrode - calomel), in applications where it is required to operate in non-aqueous solvents/solutions. Since these reference electrodes require an aqueous bridge solution (e.g. KCl NaCl), it is necessary to provide an aqueous bridge solution from the electrode and a liquid junction to the non-aqueous solvent. This is a complicated arrangement which can lead to difficulties.

The reference element of this invention can accordingly be used with advantage within a reference electrode for use in non-aqueous solutions. The skilled man will appreciate that there are a wide variety of further applications for the reference element according to this invention, including electrodes for sensing proteins, cells or viruses.

A preferred form of reference element according to this invention is silver/silver tetraphenylborate and there will now be described by way of example two methods for producing an electrode in this form.

METHOD 1

Heat platinum gauze in a hydrogen/oxygen flame to clean the surface

Dip the clean platinum gauze in silver oxide powder and flame gently until the oxygen has been removed and a greyish colour remains. Repeat this step until a sufficiently thick layer of porous silver has formed on the platinum gauze.

Electrolyse the porous silver coated platinum gauze in a saturated solution of tetraphenylborate in 1, 2 dichloroethane (or other appropriate solvent) for 12 to 18 hours at low current (approx 1 mA).

METHOD 2

Heat silver wire in a flame to clean (as above)

Electrolyse the cleaned silver wire in a saturated TPB solution for 12 to 18 hours at low current (as above)

In the case of ion selective electrodes, the membrane can be coated directly onto the Ag/AgTPB electrode. This not only provides a reversible electrode (the electronic part) without an internal aqueous filling solution, but provides ionic buffering (as well as electronic buffering) within the device.

$TPB^-$ itself can be used as an ion exchanger in ion selective electrodes. More commonly, it is also used as a counter ion with membranes using carrier-type sensing ligands (e.g. for K, $NHC_4$, Na, Ca, Mg). In these cases the membrane compositions do not need to be significantly changed for use with the internal reference electrode according to this invention. This does not mean, however, that alternative neutral carrier membranes cannot be developed with the addition of TPB.

BRIEF DESCRIPTION OF THE DRAWINGS

The invention will further be described by way of example with reference to accompanying drawings in which.

DETAILED DESCRIPTION OF THE PREFERRED EMBODIMENTS

Figure 1:
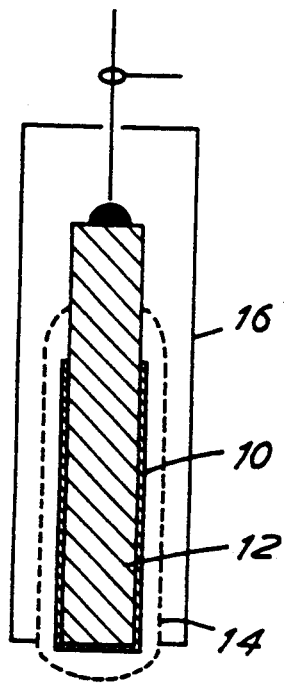
FIGS. 1, 2 and 3 are diagrams illustrating alternative forms of ion selective electrodes according to this invention.

In the arrangement shown in FIG. 1, an AgTPB coating 10 is applied to an Ag wire 12, for example by Method 2 above. An ion selective membrane 14 is then applied over the AgTPB coating and the assembly suitably encapsulated as shown at 16.

Figure 2:
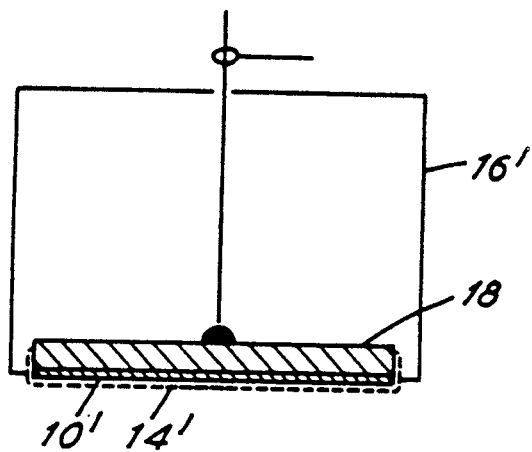

The arrangement of FIG. 2 is similar but includes a silver plate 18 in place of the silver wire of the FIG. 1 embodiment. Other components are shown with the same reference numerals, primed.

Figure 3:
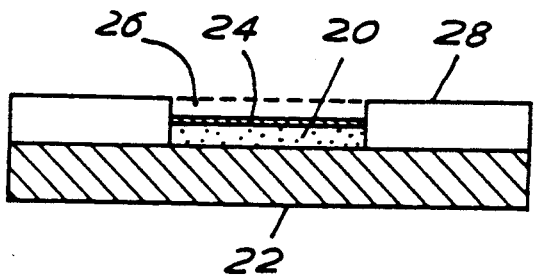

In the arrangement shown in FIG. 3, the Ag electrode is formed by an Ag film 20 suitably deposited upon a plastics or ceramic substrate 22. The AgTPB coating 24 is then applied over the Ag film so as to completely to cover the same. A permselective membrane 26 covers the AgTPB coating and a ring of encapsulation material 28 is applied so as to avoid edge effects.

Utilising the structure of FIG. 3, a plurality of ion selective electrodes may be formed on the same substrate using, for example, printing processes such as screen printing. A number of electrodes of the same selectivity may be incorporated to accommodate failure of any individual device or for the purpose of increasing accuracy by allowing simultaneous multiple measurement, with an appropriate statistical processing technique.

Alternatively, one or more of the printed electrode devices may be a reference electrode against which the potential of the working ion selective half cells may be measured. The reference electrode may be of a conventional type or may preferably be constructed in the manner of an ion selective electrode with, for example, the neutral carrier of the membrane omitted so that the electrode does not respond to the ionic species of interest and serves as a reference. It will be understood that the location in this way of the reference electrode in close proximity to the selective electrode will improve, for example, common mode rejection. Alternatively, the reference electrode may be constructed as an ion selective electrode to act additionally to null electrochemical interference. For instance, in the case where the selective electrode responds both to the ionic species of interest and to an interfering species, the reference electrode may be arranged to respond to the or each interferent.

Figure 4:
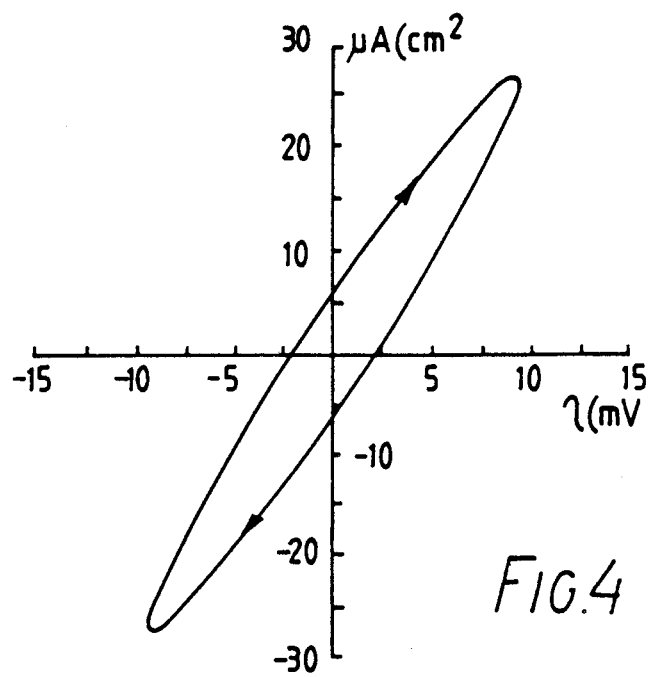
FIG. 4 is a cyclic voltamogram of an Ag/Ag TPB electrode.

Referring to FIG. 4, a cyclic voltamogram is shown, produced by varying the potential applied to a Ag/Ag TPB electrode and measuring the current. This demonstrates the reversibility of the electrode. The compressed form of the plot is explained by the low conductivity of the non-aqueous solvent solution of the TPB used in making the measurements ($10^{-3}$M tetrabutyl ammonium tetraphenyl borate in 1,2-dichloroethane).

Figure 5:
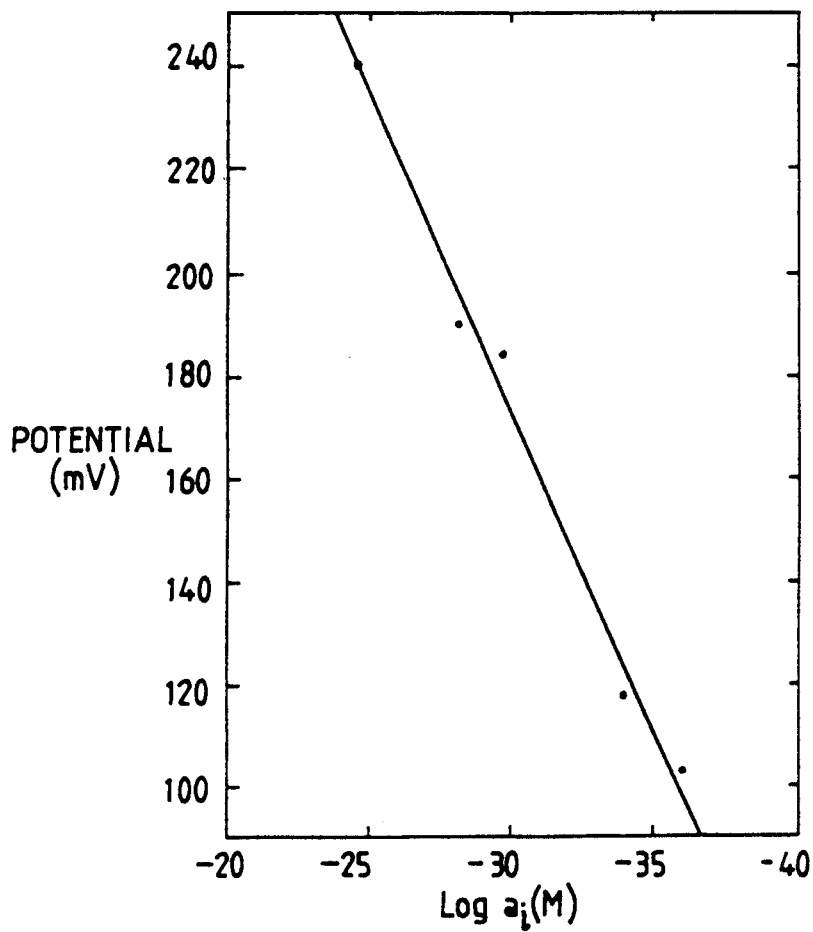
FIG. 5 is a plot of the response of an Ag/Ag TPB electrode to changes in concentration of the anion.

There is shown in FIG. 5 a plot of the measured potential of an Ag/Ag TPB electrode against concentration. Measurements were taken against a saturated calomel electrode using the tetrabutyl ammonium (TBA) cation as a bridge between the aqueous and non-aqueous phases. In particular, the cell can be defined as:

| SCE | TBACL $10^{-1}$ M (aqueous) | TBA TPB xM (dichloroethane) | Ag TPB/Ag |

The plot is "super-Nernstian" in that a slope of around $-120$ mV is observed rather than $-60$ mV as expected for a monovalent anion. This can be explained by the contribution from the activity of the TBA cation in the liquid junction equilibrium:

$$TBA^+(dichloroethane) \rightleftharpoons TBA^+(aqueous)$$

Figure 6:
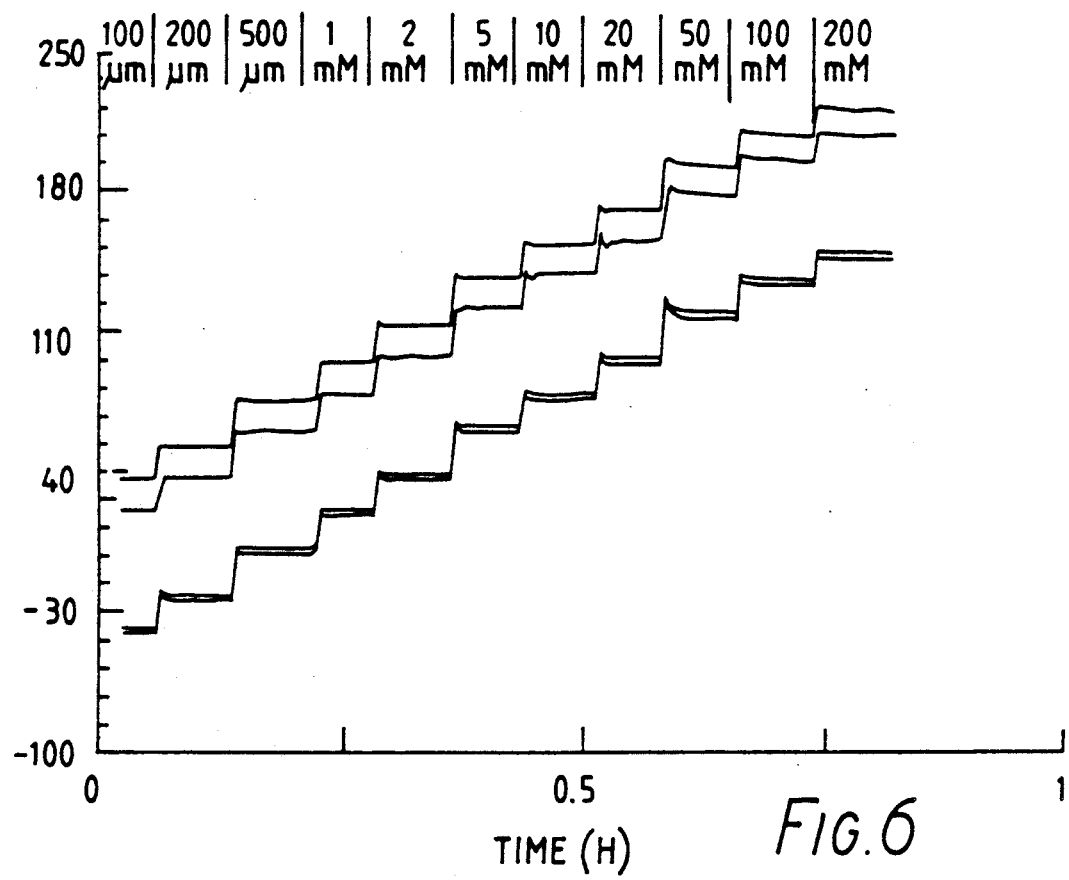
FIG. 6 shows plots of measured potential against time for respective like ion selective electrodes of the form shown in FIG. 1 in samples subject to defined step changes in ion concentration.

Using the structure illustrated in FIG. 1 and conventional membranes, ion selective electrodes according to this invention were prepared with selectivity to potassium. A batch of like electrodes was used to measure the concentration (activity) of a sample of potassium ion, the sample being subject to step-wise concentration changes. The experimental results are plotted in FIG. 6. It will be seen that the electrodes generally exhibit fast response and reasonable stability.

Figure 7:
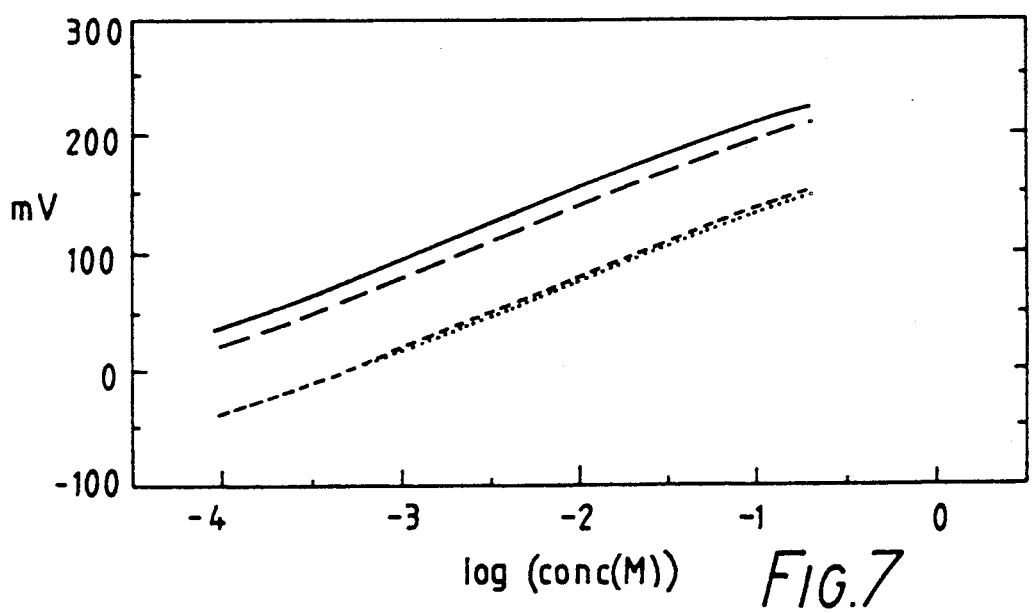
FIG. 7 is an electrode calibration plot.

FIG. 7 presents the response of the same batch of electrodes in a form in which the calibration points of the electrodes can be assessed in terms of sensitivity or slope expressed in change in potential in millivolts per decade change in concentration or activity and offset expressed in millivolts.

Ammonium, sodium, hydrogen, lithium, calcium, magnesium, nitrate, chloride, phosphate and other inorganic cation and anion selective electrodes may be constructed by coating the appropriate permselective membrane on to the Ag/AgTPB electrodes. In a similar fashion the Ag/AgTPB electrode may also be used for organic cation and anion selectivities. Electrodes based on the binding of proteins, DNA, RNA, viruses and cells to an affinity ligand incorporated into the appropriate membrane may also advantageously use the Ag-/AgTPB electrode.

This invention has been more particularly described with reference to the Ag/AgTPB electrode and this is the preferred form. It is considered, however, that TPB electrodes could be formed with other non-noble metals. Moreover, whilst TPB has the advantage of being an anion currently used within certain ion exchanger membranes, it is considered that electrodes according to the invention can usefully be constructed using other solvent soluble anions which form an insoluble salt of a metal. Preferred metal salts other than TPB are of tetrakis (4-fluorophenyl) borate, tetrakis (4-chlorophenyl) borate, dipicrylaminate, picrate and dicarbolyl cobaltate. Preferred metals in addition to silver are cadmium, cobalt, iron, lead and nickel.

We claim:

1. An electrochemical reference element in combination with an organic liquid, comprising a metal electrode and a solid electrolyte in contact with the electrode, the electrolyte comprising a salt of an organic anion with a metal cation of the electrode, the salt being substantially insoluble in said organic liquid and the anion being soluble in said organic liquid to form a solution maintaining reversible equilibrium between the anion in the electrolyte and the anion in solution in the organic liquid.

2. An element according to claim 1, wherein said anion has a hydrophobic aromatic group.

3. An electrochemical reference element comprising a metal conductor coated with a tetraphenyl borate salt of said metal.

4. An element according to claim 3, wherein the metal of the conductor is selected from the group consisting of silver, cadmium, cobalt, iron, lead and nickel.

5. An element according to claim 4, wherein the metal of the conductor is silver.

6. An ion selective electrode comprising an electrochemical reference element according to claim 3 with an ion selective membrane containing tetraphenyl borate ion and establishing direct contact with said coating.

7. An electrochemical reference element comprising a metal conductor coated with a salt of said metal selected from the group consisting of tetrakis (4-fluorophenyl) borate, tetrakis (4-chlorophenyl) borate, dipicrylaminate, picrate and dicarbolyl cobaltate.

8. An electrochemical reference element comprising a metal electrode and a solid electrolyte in contact with the electrode, the electrolyte comprising a salt of a metal cation from the metal electrode and an anion selected from the group consisting of:

(a) anions of the formula $(ArO)_4B^-$ wherein each ArO group, which may be the same or different, represents an aryloxy group having up to 20 carbon atoms optionally substituted by one or more halogen atoms or nitro groups, and (b) anions of hydroxy-substituted aromatic compounds.

9. An element according to claim 8, wherein the aryl group Ar is phenyl or naphthyl which may be substituted by one or more hydrocarbyl groups having up to 6 carbon atoms.

10. An element according to claim 9, wherein Ar is phenyl and 4-halo phenyl.

11. An element according to claim 8, wherein said anion is selected from the group consisting of phenols and substituted phenols and naphthols and substituted naphthols.

12. An element according to claim 8, wherein the metal of the electrode is selected from the group consisting of silver, cadmium, cobalt, iron, lead and nickel.

13. An ion selective electrode comprising a reference element according to claim 8 with the solid electrolyte establishing contact with an ion selective membrane.

14. An element according to claim 8, wherein said anion is selected from the group consisting of mono-hydroxy phenols and mono-hydroxy naphthols, each of which may contain one or more electron withdrawing groups.

15. An ion selective electrode comprising a metal electrode, a solid electrolyte coating on the metal electrode, the electrolyte comprising a salt of an organic anion with the metal cation of the electrode and an ion selective membrane in direct contact with the solid electrolyte coating, the membrane including said organic anion.

16. An ion selective electrode according to claim 15, wherein said organic anion is selected from the group consisting of:

(a) anions of the formula $(ArO)_4B^-$ wherein each ArO group, which may be the same or different represents an aryloxy group having up to 20 carbon atoms optionally substituted by one or more halogen atoms or nitro groups, and (b) anions of hydroxy-substituted aromatic compounds.

17. An ion selective electrode according to claim 16, wherein said organic anion is tetraphenyl borate.

* * * * *